(12) United States Patent
Willing et al.

(10) Patent No.: US 7,636,153 B2
(45) Date of Patent: Dec. 22, 2009

(54) GAS SENSOR

(75) Inventors: Bert Willing, Blonay (CH); Markus Kohli, Grandson (CH); Andreas Seifert, Denens (CH)

(73) Assignee: IR Microsystems SA, Lausanne (CH)

( * ) Notice: Subject to any disclaimer, the term of this patent is extended or adjusted under 35 U.S.C. 154(b) by 193 days.

(21) Appl. No.: 11/840,324

(22) Filed: Aug. 17, 2007

(65) Prior Publication Data

US 2008/0198364 A1     Aug. 21, 2008

(30) Foreign Application Priority Data

Feb. 21, 2007    (EP) .................................. 07003553

(51) Int. Cl.
*G01N 21/39* (2006.01)
*G01N 21/00* (2006.01)
*G01N 21/35* (2006.01)

(52) U.S. Cl. .................. 356/72; 356/432; 356/437; 356/73; 250/339.13

(58) Field of Classification Search ............... 356/432, 356/72, 73
See application file for complete search history.

(56) References Cited

U.S. PATENT DOCUMENTS 3,820,901 A    6/1974   Kreuzer
4,808,828 A *   2/1989   Kitamori et al. ......... 250/458.1
4,871,916 A    10/1989   Scott
5,178,836 A *   1/1993   Kitamori et al. ............. 422/73
2003/0038237 A1   2/2003   Webber
2005/0160800 A1   7/2005   Schindler et al.

FOREIGN PATENT DOCUMENTS

AU    549 570 B2    1/1986
EP    1 154 932    7/2005
WO    2005/026705    3/2005

OTHER PUBLICATIONS

European Search Report for corresponding Application No. 07 00 3553 dated Jun. 24, 2007.

* cited by examiner

*Primary Examiner*—F. L Evans
(74) *Attorney, Agent, or Firm*—Renner, Otto, Boisselle & Sklar, LLP

(57) ABSTRACT

A combined gas sensor device allowing the measuring of the concentration of a gas by tunable diode laser spectrometry as well as by resonant photo-acoustics within one housing. A laser beam used for laser spectrometry is sent across the openings of a measuring cell usually used for resonant photo-acoustic determination. Thus, both measuring principles use the same gas sensing module with a minimum of space consumption, so that the device can be produced with minimum dimensions. Further, a common opto-electronics and electronics platform can be used which reduces the overall costs of such a combined gas sensor.

22 Claims, 3 Drawing Sheets

GAS SENSOR

This nonprovisional application claims priority under 35 USC §119(a) to European Patent Application No. 07 003 553.0 filed on Feb. 21, 2007, the entire contents of which are hereby incorporated by reference.

TECHNICAL FIELD OF THE INVENTION

The present invention refers to a combined infrared (IR) gas sensor device for measuring the concentration of a target gas by using either tunable diode laser spectrometry (TDLS) or photo-acoustical (PA) detection.

DESCRIPTION OF THE RELATED ART

Both tunable diode laser spectrometry (TDLS) and photo-acoustical (PA) detection measurement techniques are well known in the prior art. TDLS is disclosed, for example, in EP 1 549 932 B1. Photo-acoustic sensors are disclosed in numerous patent applications.

Both measurement techniques have their fields of application and both work with a specific sample cell design. TDLS needs an absorption path were the intensity of the absorbed light is measured by a photo sensor, for example a photo-diode. The absorption path can be closed in a sample cell or open without any housing defining the absorption volume of the gas to be detected. The lengths of the absorption path greatly determines the achieved sensitivity and the environment influences the diffusion velocity, which means, that longer diffusion periods cause slower reaction times of the system. However, an open environment is subject to greater external influences.

PA requires an acoustically closed measuring cell, where the absorption of light by the target gas leads to the generation of a sound pressure, which is picked up by a microphone. The use of a diode laser as a light source for PA allows modulating the light beam at high frequencies (kilohertz (kHz) to megahertz (MHz)), which is not feasible with conventional thermal light sources. This kHz modulation enables the use of resonant PA (RPA), where the frequency of the modulation is adjusted, so that an acoustic resonance frequency of the sample volume within the measuring cell is matched. The design of the measuring cell influences the resonance frequency of the sample volume. In such a resonant measuring cell, the maxima (anti-nodes) and minima (nodes) of the sound pressure are precisely localized. The sound is picked up at the anti-node and the measuring cell can be left open at the locations of the node. Depending on the design of the measuring cell, the sound pressure anti-nodes are different.

Thus, TDLS and RPA techniques each have their own sets of target gases. TDLS measures simple gases highly selectively and with a very high sensitivity (i.e. toxic gases in the ppm range), whereas RPA is more appropriate to measure large molecules with broad absorption features where the required detection limit is about an order of magnitude higher (i.e. hydrocarbon in the 100 ppm range). However, in some cases a set of gas sensors is required to be housed in a single instrument, which requires both TDLS and RPA techniques (i.e. a combined sensor for toxic and combustible gases).

Thus, there is a strong need in the art for a combined sensor, which can be housed in a single instrument that uses either TDLS or RPA techniques according to the respective gas to be detected.

SUMMARY OF THE INVENTION

The gas sensor device of the present invention addresses such need and offers additional advantages as discussed herein.

According to the invention the IR gas sensor device comprises at least one first tunable laser source and at least one second tunable laser source both generating a first and a second, respectively, modulated laser beam providing a first and second, respectively, measuring path. The gas sensor device further comprises first and second detection means associated to the first and second measuring path, respectively, wherein the first detection means is an optical sensor receiving the first laser beam and the second detection means is an acoustical sensor. Additionally the gas sensor device comprises at least one measuring chamber for providing an absorption volume for a target gas to be detected, wherein the measuring chamber comprises different openings for the first and second measuring path and at least second detection means. Further included are electronic processing means for controlling the laser sources and providing resulting measurement signals.

The present invention makes use of the geometrical distribution of nodes and anti-nodes in a RPA cell in order to create a combined TDLS-RPA measuring chamber. The laser beam of the TDLS laser is collimated and sent through the open slots of the measuring chamber which is designed to be used for RPA measurement by providing a respective gas volume, an assigned opening for the second laser beam and a respective acoustical sensor, for example microphone. Dependent on the requirements for the TDLS, the laser beam having passed the measuring chamber can be detected by a respective photo sensor, for example photodiode, or can be reflected back through the measuring chamber by an appropriate mirror to a photodiode arranged near the first laser source. Further, it is possible to provide more passes of the first laser beam through the measuring chamber. The openings in the measuring chamber might be circular or in form of a slot, for example. For multi passes the slot form is preferred. The second laser beam provided by the second laser source (for example diode laser), which is used for the RPA detection is entered into the respective opening of the measuring chamber and excites the gas volume of the measuring chamber at the chamber's acoustic resonance. If the acoustic eigenmode is chosen appropriately, the measuring chamber can be left open or can comprise respective openings for TDLS.

A usual design is a cylindrical measuring chamber with a basic longitudinal resonance having a lower frequency. It is also possible, for example, to design a measuring chamber having in comparison with the cylindrical measuring chamber, a relatively short length and a greater diameter. In the latter the sound pressure anti-nodes are organized as lobes in a first and second longitudinal half of the chamber. The resonance frequency of such a design is higher than of a design of a cylindrical measuring chamber having a greater length in comparison to the diameter. However, all designs are possible providing nodes and anti-nodes within in the sample volume in longitudinal, radial, axial or other directions.

In a further embodiment for special application of gas detection, only one common diode laser source is used for different kinds of laser beams for providing a first measuring path and a second measuring path through one common opening. The diode laser is switched (multiplexed) between the two conditions being necessary to generate a laser beam for a TDLS path or a RPA path, respectively. It is possible to reflect the first laser beam after having traveled through the gas volume from the respective wall of the chamber back through the entry opening or to use a photo sensor instead. This arrangement is preferred for the measurement of gases, which can be detected on a path length being in the same order, e.g. the measurement of methane with TDLS and hydrocarbons with RPA detection.

In a preferred embodiment, the dimensions of the measuring chamber are adapted to provide sound pressure anti-nodes, which are organized as lobes in the upper and lower half of the chamber. Additionally the openings of the firth path are arranged at the belt line between the lobes.

In general, more than one measuring chamber can be introduced into the first measuring path for TDLS, or the measuring chamber used for RPA detection can be introduced into a larger second measuring chamber, which is used for TDLS. The advantage of the invention is, that TDLS and RPA detection can be performed in a common enclosure and with a common optoelectronics and electronics platform. The measuring chamber used for RPA detection can be freely positioned along the TDLS absorption path (first measuring path) without any interference between TDLS and RPA measurement. The use of the same enclosure (i.e. for explosive or environmental protection) and the same electronics platform drastically reduces the overall costs of such a combined gas sensor.

An aspect of the invention is, to send a TDLS laser beam (first laser beam) across the openings of a measuring chamber which is used for RPA detection to make use of TDLS and RPA detection in the same gas sensing module, with minimum dimensions.

According to a further embodiment of the invention the modulation frequency of the second modulated laser beam is matched to the acoustic resonance frequency of the volume of the measuring chamber.

In a further embodiment the measuring chamber is cylindric with openings for the first and second measure path at the front sides.

Further features and advantages of the invention can be obtained from the following description of preferred embodiments in connection with the claims and the drawings. The single features can be realized alone or in combination in embodiments of the inventions.

DETAILED DESCRIPTION OF THE INVENTION

Figure 1:
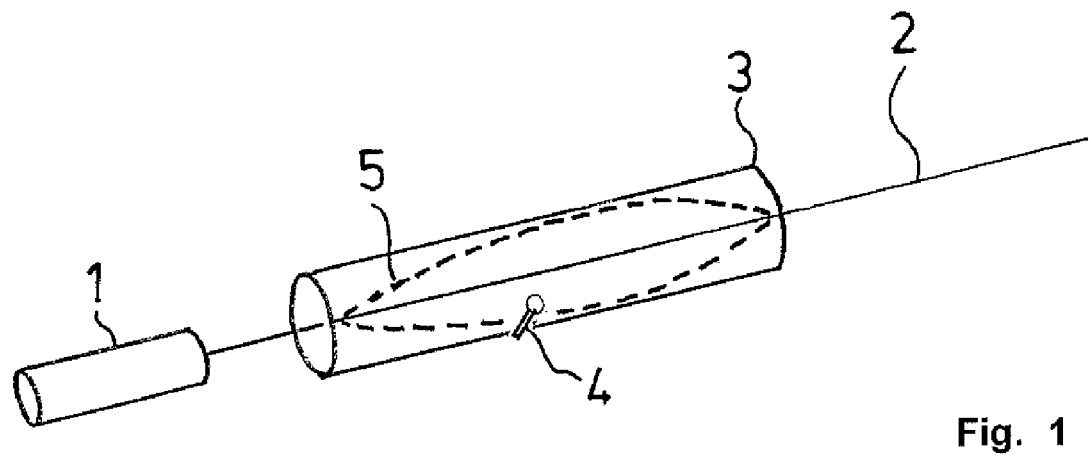
FIG. 1 a basic cylindrical sample cell arrangement for RPA.

In the example in FIG. 1 a laser source 1 provides a laser beam 2 passing through a cylindrical measuring chamber of, for example, 4 cm lengths and 0.5 cm diameter, thereby providing a basic longitudinal resonance. The chamber also comprises as usual a microphone 4. The amplitude of the sound pressure is indicated by dotted line 5. The resonance frequency of such an arrangement is approximately 4 kHz.

Figure 2:
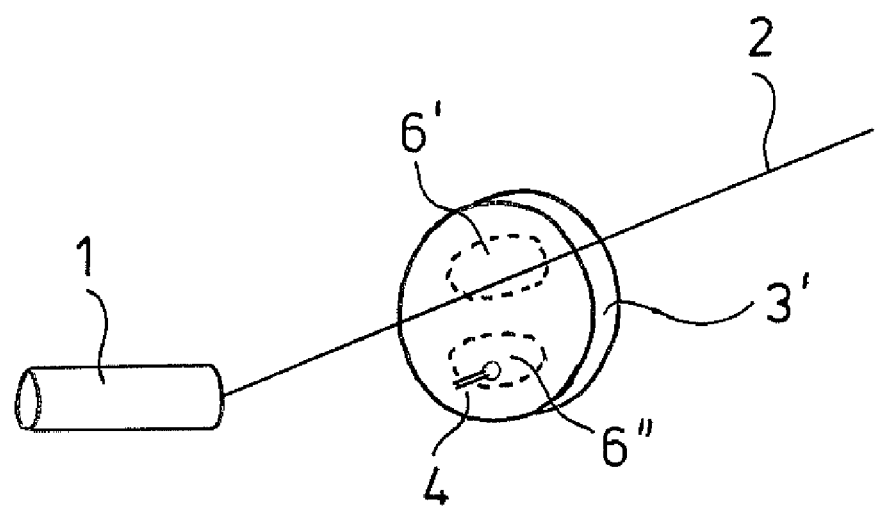
FIG. 2 an arrangement for the purpose of a fast diffusion of the target gas into the sample cell for RPA.

In an azimuthal design as shown in FIG. 2, the length of the chamber is for example 0.6 cm and the diameter 2 cm. This design provides sound pressure anti-nodes as lobes in 6' on 6" in the upper and lower half of the chamber 3'. The resonance frequency of this design is approximately 10 kHz.

Figure 3:
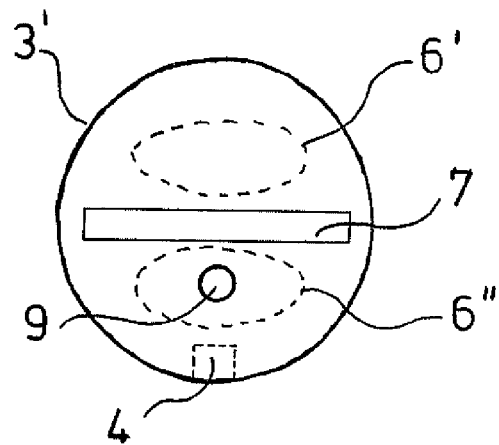
FIG. 3 the arrangement of the openings in a measuring chamber design according to FIG. 2.
Figure 4:
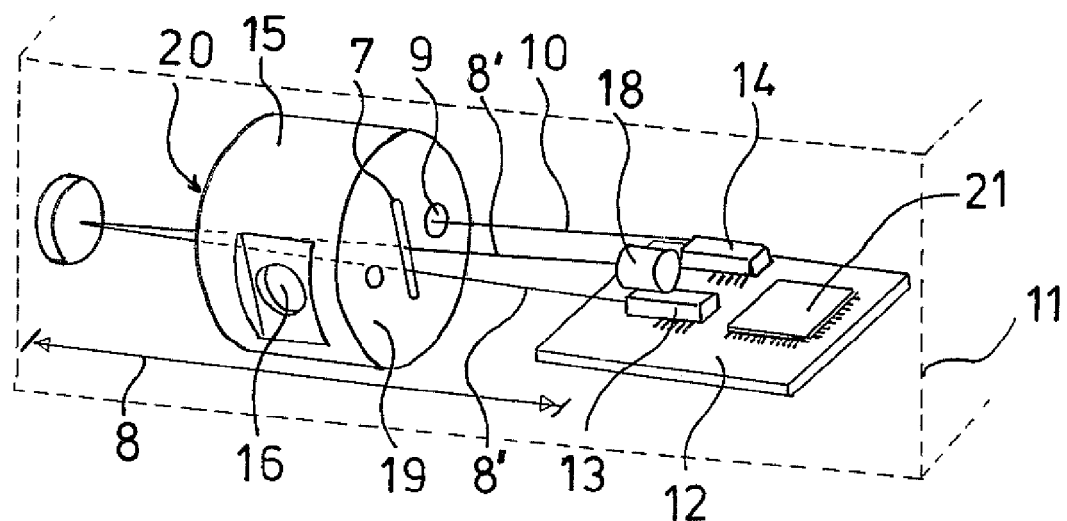
FIG. 4 a principle representation of a IR gas sensor device.

FIG. 3 shows a front view of a detection chamber 3' according to FIG. 2, where the front and back sides are identical. The upper node 6' and the lower node 6" enables an opening at the belt line of the measuring chamber 3' as shown in this figure. The opening 7 along the belt line is used for gas inlet and outlet and for a laser beam for a TDLS measuring path 8 as shown in FIG. 4. Opening 9 is used for the RPA measuring path 10 as shown in FIG. 4.

FIG. 4 shows the principle arrangement of the infrared gas sensor device with a housing 11 only indicated by dotted lines which includes an electronic board 12 on which are arranged a first tunable laser diode 13, a second tunable laser diode 14, a microprocessor 21 and other electronic components for the function of the device. Further shown is a measuring chamber 15 with a slot 7 on the front side 19 as well as on the back side 20 (not shown). The chamber 15 further comprises an opening 9 on the front side 19 faced to the second laser 14. The reference number 16 refers to a port for a microphone adjacent the inner volume of the chamber 15. Remote from the chamber 15, in this embodiment, there is a mirror 17 for reflecting the laser beam 8' emitted by the first laser source 13. The reflected laser beam 8' travels again through the slots 7 back to a laser diode 18 arranged above the first laser source 13.

Second laser source 14 provides a laser beam 10' which enters via opening 9 the measuring chamber 15 for exciting the gas volume inside the chamber 15.

Figure 5:
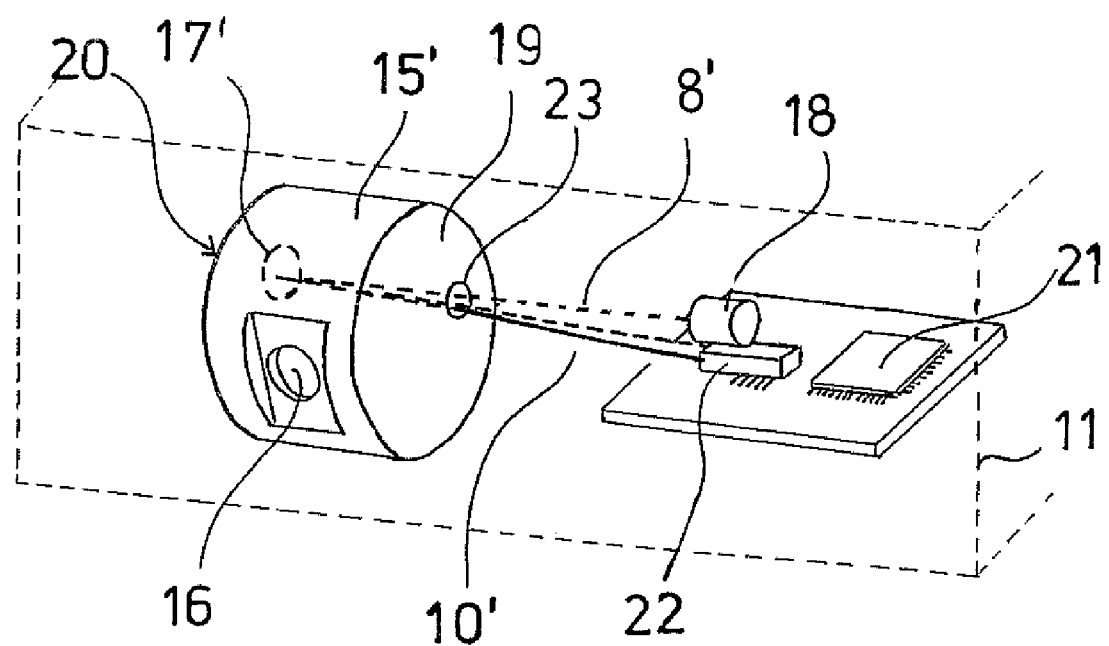
FIG. 5 another principle representation of a IR gas sensor device with only one diode laser source.

FIG. 5 shows an arrangement with only one tunable diode laser source 22 which is multiplexed between two different beam generating conditions for providing either a laser beam for the TDLS measuring path or the RPA measuring path. Both laser beams enter the measuring chamber 15' via the same opening 23. While the laser beam 8', which is modulated for TDLS is reflected back by a mirror 17' inside the housing 15', the other laser beam 10', which is modulated for RPA detection only enters the opening 23 and excites the gas volume inside the chamber 15'. In this embodiment the RPA beam also generates upper node 6' and lower node 6" of FIG. 3 since it enters the housing 15' via the off-center opening 23.

As mentioned above, with this device a common housing 11 with a common optoelectronics and electronics platform 12, TDLS and RPA detection can be performed on the same place in the housing 11. The embodiment as shown is only for the purpose of explanation and not limited to the special design.

The invention claimed is:

1. A combined infrared (IR) gas sensor device for measuring the concentration of different target gases by using either tunable diode laser spectrometry (TDLS) or photo-acoustical (PA) detection comprising:

at least one first tunable laser source generating a first modulated laser beam providing a first measuring path;

at least one second tunable laser source generating a second modulated laser beam providing a second measuring path;

first and second detection means associated to said first and second measuring path, respectively, wherein said first detection means is an optical sensor receiving said first laser beam, and said second detection means is an acoustical sensor;

at least one measuring chamber for providing an absorption volume for a target gas to be detected, said measuring chamber comprises different openings for said first and second measuring path, and at least said second detection means; and electronic processing means for controlling said laser sources and providing resulting measuring signals.

2. A device according to claim 1, wherein said first tunable laser source and said second tunable laser source are only one diode laser, which either generates said first modulated laser beam providing said first measuring path or generates said second modulated laser beam providing said second measuring path.

3. A device according to claim 1, wherein said measuring chamber comprises opposite openings arranged in the first measuring path, thus allowing the first laser beam to travel at least once through the measuring chamber.

4. A device according to claim 3, wherein said first detection means is arranged remote from said at least one measuring chamber.

5. A device according to claim 3, wherein said measuring chamber is cylindrical with openings for the first and second measuring path at the front side and at least one opening for the first measuring path at the back side.

6. A device according to claim 1, wherein the dimensions of the measuring chamber are adapted to provide sound pressure anti-nodes, which are organized as lobes in a first and second longitudinal half of the chamber.

7. A device according to claim 6, wherein the openings of the first path are arranged at a line between the lobes.

8. A device according to claim 1, wherein the modulation frequency of the second modulated laser beam is matched to the acoustic resonance frequency of said measuring chamber.

9. A combined IR gas sensor device for measuring the concentration of different target gases by using either tunable diode laser spectrometry (TDLS) or photo-acoustical (PA) detection comprising at least one tunable laser source for generating a first modulated laser beam providing a first measuring path, and a second modulated laser beam providing a second measuring path;

first and second detectors associated to said first and second measuring path, respectively, wherein said first detector is an optical sensor receiving said first modulated laser beam, and said second detector is an acoustical sensor;

a measuring chamber for providing an absorption volume for a target gas to be detected, said measuring chamber comprising at least one opening for said first and second measuring path, and at least said second detection means; and an electronic controller to control said at least one tunable laser source and provide resulting measuring signals.

10. A device according to claim 9, wherein the at least one tunable laser source comprises a same laser source that generates both the first modulated laser beam and the second modulated laser beam.

11. A device according to claim 9, wherein the at least one tunable laser source comprises a first and second different laser sources that generate the first and second modulated laser beams, respectively.

12. A device according to claim 9, wherein the at least one opening comprises a same opening through which the first and second measuring paths both extend.

13. A device according to claim 9, wherein the at least one opening comprises first and second different openings through which the first and second measuring paths extend, respectively.

14. A device according to claim 9, wherein the first and second measuring paths are at least partially coincident.

15. A device according to claim 14, wherein the first and second measuring paths are coincident about at least a majority of their respective lengths.

16. A method for measuring the concentration of different target gases using at least one tunable laser source and a measuring chamber for providing an absorption volume for a target gas to be detected, comprising:

generating a first modulated laser beam along a first measuring path included at least in part within the measuring chamber, and generating a second modulated laser beam along a second measuring path included at least in part within the measuring chamber, using the at least one tunable laser source;

optically sensing said first modulated laser beam along the first measuring path, and acoustically sensing a result of said second modulated laser beam within the measuring chamber;

providing measuring signals as a result of the optically sensing and the acoustically sensing.

17. The method of claim 16, wherein the first modulated laser beam and the second modulated laser beam are generated by the a same tunable laser source.

18. The method of claim 16, wherein the first modulated laser beam and the second modulated laser beam are generated by respective different tunable laser sources.

19. The method of claim 16, wherein the measuring chamber comprises at least one opening through which the first measuring path and the second measuring path extend into the measuring chamber.

20. The method of claim 19, wherein the at least one opening comprises a same opening through which the first measuring path and the second measuring path extend into the measuring chamber.

21. The device of claim 1, the components of which are comprised within a common enclosure.

22. The device of claim 9, the components of which comprised within a common enclosure.

* * * * *